(12) United States Patent
Hermosa Prieto et al.

(10) Patent No.: US 6,890,530 B2
(45) Date of Patent: May 10, 2005

(54) **COMPOSITION COMPRISING FUNGI OF GENUS *TRICHODERMA* USED AS BIOLOGICAL CONTROL AGENT AND THE APPLICATIONS THEREOF**

(75) Inventors: Maria Rosa Hermosa Prieto, Salamanca (ES); Isabel Grondona España, Salamanca (ES); Antonio Llobell Gonzalez, Seville (ES); Enrique Monte Vazquez, Seville (ES)

(73) Assignees: Newbiotechnic, S.A., Seville (ES); Universidad de Salamanca, Salamanca (ES)

( * ) Notice: Subject to any disclaimer, the term of this patent is extended or adjusted under 35 U.S.C. 154(b) by 202 days.

(21) Appl. No.: 10/258,267

(22) PCT Filed: Apr. 27, 2001

(86) PCT No.: PCT/ES01/00166

§ 371 (c)(1),
(2), (4) Date: Jan. 22, 2003

(87) PCT Pub. No.: WO01/84935

PCT Pub. Date: Nov. 15, 2001

(65) Prior Publication Data

US 2004/0176249 A1 Sep. 9, 2004

(30) Foreign Application Priority Data

Apr. 28, 2000 (ES) .............................. 20001098

(51) Int. Cl.$^7$ ......................... A01N 63/04; A01N 63/00; C12N 1/14
(52) U.S. Cl. ................. 424/93.5; 424/254.6; 424/254.1
(58) Field of Search .......................... 424/254.1, 254.6, 424/93.5

(56) References Cited

U.S. PATENT DOCUMENTS

| 4,915,944 | A | * | 4/1990 | Chet et al. .................. 424/93.5 |
| 4,996,157 | A | * | 2/1991 | Smith et al. ............... 424/93.5 |
| 5,084,272 | A | * | 1/1992 | Speakman et al. ......... 424/93.5 |
| 5,288,634 | A | * | 2/1994 | Harman et al. ........... 435/254.1 |
| 5,314,691 | A | * | 5/1994 | Coffey et al. .............. 424/93.5 |
| 5,422,107 | A | * | 6/1995 | Kubota ....................... 424/93.5 |
| 6,228,806 | B1 | * | 5/2001 | Mehta ........................ 504/117 |
| 6,475,772 | B1 | * | 11/2002 | Kalra et al. .............. 435/254.6 |
| 6,750,176 | B2 | * | 6/2004 | Misumi et al. ............. 504/117 |

FOREIGN PATENT DOCUMENTS

| EP | 0466133 A2 | * | 1/1992 | .......... A01N/63/04 |
| ES | 2109182 | | 1/1998 | |
| JP | 11225745 | | 8/1999 | |
| JP | 11253151 | | 9/1999 | |

OTHER PUBLICATIONS

Ryoji, Fukuda; Abstract of JP 04–29905; Jan. 31, 1992.*
Kubota et al; Abstract of JP 09–087122; Mar. 31, 1997.*
Harman et al; AN 94:21892 AGRICOLA, Combining effective strains of Trichodema harzianum and solid matrix priming to improve biological seed treatments, 1989, Plant Disease, 73(8), 631–637.*
Devay et al; AN 97:40167 AGRICOLA, Comparisions of gliocaldium virens and a combination of Trichiderma species in polymer coatings of cotten seed for controlling diseases, 1996, Proceedings, vol. 1, 272–273.*
Chen C. y McBeath J. H. "Effects of Trichoderma atroviride on Phythium damping off of pea" Phytopatology 1993 vol. 83(12), p. 1347.
McBeath et al. "Evaluation of Trichoderma atroviride in controlling black scurf of Potatoes under Comercial Field" Phytopatology 1993. vol. 83(12), p. 1347.
McBeath et al. "Control of Petunia Sclerotinia stem rot with Trichoderma atroviride" Phytopatology 1996. vol. 86(11; suplemento), pp. 37–38.
Hong, C. et al., "Effects of Wounding, Inoculum Density, and Biological Control Agents on Postharvest Brown Rot of Stone Fruits" Pleant Disease 1998. vol. 82(11), pp. 1210–1215.
Tatagiba, et al. Biological control of Botrytis cinerea in Residues and Flowers of Rose (Rosa hybrida) Phytoparasitica, 1998. vol. 26(1), pp. 1–12.
Dodd, S. L. et al "Examination of Trichoderma Phyologenies derived from Ribosomal DNA sequence data" Micol. Research 2000. vol. 104 (1), pp. 23–34.
Hermosa, M.R. et al. "Molecular Characterizacion and Identification of Biocontrol Isolates of Trichoderma spp." Applied and Environmental Microbiology, 2000. vol. 66(5), pp. 1890–1998.
Thrane, C. et al. "Substrate colonizacion, strain competition, enzyme production in vitro, and biocontrol fo Pythium by Thrichoderma spp. Isolates P1 and T3" European Journal of Plant Pathology, 2000. vol. 106, pp. 215–225.

* cited by examiner

*Primary Examiner*—Sabiha N. Qazi
(74) *Attorney, Agent, or Firm*—Harrison & Egbert

(57) ABSTRACT

The composition includes fingi belonging to one or more species of fungi of the genus *Trichoderma*, selected from *T. asperellum*, *T. atroviride*, *T. inhamatum* and their mixtures, useful as an agent for the biological control of phytopathogenic organisms. The composition is suitable for protecting or treating plants and plant material against infections and diseases caused by plant pathogens, and/or to stimulate plant growth, and/or to induce systemic resistance in plants to diseases caused by phytopathogenic organisms, and/or to control biodeterioration agents of materials.

9 Claims, No Drawings

COMPOSITION COMPRISING FUNGI OF GENUS *TRICHODERMA* USED AS BIOLOGICAL CONTROL AGENT AND THE APPLICATIONS THEREOF

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention refers to a composition which comprises fingi belonging to the genus *Trichoderma*, useful as an agent for the biological control of plant pathogens, suitable for protecting or treating plants and plant material against infections and diseases caused by phytopathogenic organisms, and/or to stimulate plant growth, and/or to induce systemic resistance to disease in plants, and/or to control biodeterioration agents of materials.

BACKGROUND OF THE INVENTION

The most common methods employed to control pathogens of plants of agronomic or horticultural interest include the use of large amounts of chemical products (fungicides, pesticides, etc.), some of which are classified as carcinogens and/or are toxic to animals and plants. Additionally, some pathogens can become resistant to said chemical products, making impossible their future use.

Biological control of phytopathogenic organisms constitutes a more attractive alternative than that involving chemical products. This alternative comprises the use of biological control agents which exist in nature and are in fact the natural enemies of the phytopathogenic organisms to be controlled. Biological control agents (live organisms and compounds produced by said organisms) are safer, more biodegradable and less deleterious to the environment than the chemical compounds usually employed to protect or treat plant diseases. However, the use of said biological control agents has been hindered by different causes, including the inadequate identification of biological control agents, which brings about reproducibility problems. One of the most important agents for the biological control of plant pathogens are the fungi belonging to the genus *Trichoderma*, some of which are capable of controlling a wide range of phytopathogenic organisms of great importance in agriculture. However, despite the relative success achieved, it has not yet been possible to reach the desired levels of control of plant diseases.

BRIEF SUMMARY OF THE INVENTION

The invention tackles the problem of searching for a new biological control agent with the object of increasing the arsenal of biological remedies for controlling agents which cause infections and diseases in plants and plant material and/or biodeterioration (biofouling) of materials.

The solution put forward by this invention is based on the fact that the inventors have identified species of fungi belonging to the genus *Trichoderma*, which are useful as biological control agents, the mixture of which produce an improved effect in the biological control of phytopathogenic organisms.

Consequently, the object of the present invention is constituted by a composition which comprises fungi of the genus *Trichoderma*, selected from fungi belonging to the species *T. asperellum, T. atroviride, T. inhamatum* and mixtures thereof, useful as biological control agents of plant pathogens. The use of said composition to protect or to treat plants and plant material against infections and diseases caused by phytopathogenic organisms, and/or to stimulate plant growth, and/or to induce systemic resistance to diseases caused by phytopathogenic organisms in plants, and/or to control biodeterioration agents of materials, constitute additional objects of the present invention.

DETAILED DESCRIPTION OF THE INVENTION

The invention provides a composition useful as a biological control agent, from now on referred to as the composition of the invention, which comprises fungi belonging to one or more species of the genus *Trichoderma*, selected among *T. asperellum, T. atroviride, T. inhamatum* and mixtures thereof.

As employed in this description, the term "biological control" refers to the control of a pathogenic organism by the use of a second organism, and includes both the second organism per se as well as the products of said second organism which are capable of controlling pathogens, which may be isolated and applied directly onto the plant, to the plant material or to the soil, or otherwise, the second organism can be administered so that it produces said pathogen control compounds in situ.

According to the length and composition of the nucleotide sequences of the intergenic regions [ITS], the species *T. asperellum* is defined by the sequence AJ224021 [access code in the database of the EMBL (European Molecular Biology Laboratory) of strain IMI 20268 [International Mycological Institute (IMI), U.K.], while species *T. atroviride* is defined by the sequence AJ224009 (EMBL) of strain IMI 281112, and species *T. inhamatum* is defined by sequence Z68187 (EMBL) of the type strain CBS 273.78 [Centraalbureau voor Schimmelcultures, Netherlands].

In a specific embodiment, the composition of the invention comprises, at least, two fungi belonging to different species of the genus *Trichoderma* selected from among *T. asperellum, T. atroviride* and *T. inhamatum.*

In another specific embodiment, the composition of the invention is formed by a mixture of fungi belonging to the species *T. asperellum, T. atroviride* and *T. inhamatum.*

The composition of the invention may also contain, if desired, one or more additional biological control agents, chosen among fungi belonging to species of the genus *Trichoderma* different from the species *T. asperellum, T. atroviride* or *T. inhamatum*, fungi belonging to other genera, bacteria and mixtures thereof, as long as they are not incompatible with the fungi present in the composition of the invention.

The composition of the invention can be presented in any form of presentation suitable for its administration or application, for example, in solid or liquid form. Liquid presentation forms are suitable for their pulverisation on soil, the plant or upon plant material, or otherwise, to make a bath in which to submerge the plants or plant material.

The composition of the invention can be applied by any conventional method. In a specific embodiment, the composition of the invention is applied by pulverisation upon soil, the plant or plant material, or by pilling the seeds, or otherwise by immersion of the plant or plant material in a bath containing the composition of the invention.

The composition of the invention may be obtained by conventional methods by mixing the fungi present in the composition of the invention.

Several tests have shown that the composition of the invention is useful in protecting or treating plants and plant material against infections and diseases caused by phytopathogenic organisms, and/or to stimulate plant growth, and/or to induce systemic resistance to diseases caused by phytopathogenic organisms in plants, and/or to control biodeterioration agents of materials.

In all cases the effect of the composition of the invention has been determined in terms of increase in yield, as protection conferred by said composition of the invention against phytopathogenic organisms has been demonstrated by the antagonistic effects in in vitro culture, in which the species of *Trichoderma* constituting the composition of the invention reduced the development of different phytopathogenic organisms by means of mycoparasitism (hydrolytic enzymes) and antibiosis (inhibition of the growth of the phytopathogenic organism by metabolites produced before there is contact between the colonies).

The invention provides a method to protect or treat plants and plant material against infections and diseases caused by plant pathogens which comprises the application of an effective amount of the composition of the invention, either onto the soil, the plant or plant material to be protected or treated.

In the sense used in this description, the term "effective amount" refers to the sufficient amount to obtain the beneficial or desired results. An effective amount can be administered in a single operation or in several administrations. In terms of treatment or protection, a "sufficient amount" is the amount sufficient to palliate, improve, stabilise, revert, retard or delay the progression of the stages of diseases caused by plant pathogens.

The ability of the composition of the invention to protect or treat plants or plant material against infections and diseases caused by phytopathogenic organisms has been shown by different tests, such as protection or treatment of rhizomania of beet and of the infection caused by the fungus *Rhizoctonia solani* in sugar beet crops, in the protection or treatment of strawberry crops at the level of greenhouse plants and in the protection or treatment of melon collapse.

The protection of the sugar beet crop against beet necrotic yellow vein virus (BNYVV) which causes rhizomania in beet has been tested by antagonistic action against its vector, the fungus *Polymyxa betae*, and the increase in yield has been expressed in terms of number of seedlings and amount of sugar produced per unit surface (metric tons (Tm) of sugar/Ha). The application of the composition of the invention has been carried out by pulverisation on the soil by seed pilling.

Protection of sugar beet crops against the fungus *Rhizoctonia solani* has been studied in tests carried out in fields with the presence of the pathogen, and the yield of the crop was expressed in terms of the number of seedlings and amount of sugar produced per unit surface (Tm of sugar/Ha).

Protection of strawberry crop, at the plant nursery level, has been studied by pulverisation on soil and immersion of the strawberry plants to protect or treat in a solution which comprises the composition of the invention, and a study has been carried out on the influence of the composition of the invention upon the precocity of a specific phenotypic state, as well as upon the production of commercial plants. The results obtained with the composition of the invention have been compared with those obtained with other strains of other species of *Trichoderma*.

Protection of melon crops against the pathogens causing melon collapse, *Acremonium* sp. and *Monosporascus* sp., by the use of a composition of the invention, has been studied both in sterile soil and in soil containing the pathogen, with the corresponding controls, being it possible to observe, in all cases, a far superior root development (rooting) in the plants which were treated with the composition of the invention than in the control plants.

The invention also provides a method to stimulate plant growth which comprises applying an effective amount of the composition of the invention either onto the soil or on the plants the growth of which wants to be stimulated.

The ability of the composition of the invention to stimulate plant growth has been shown by a test directed towards determining the increase in yield of strawberry crop by means of the measurement of first class commercial fruits. The application of the composition of the invention is carried out by pulverisation of the soil and by immersion of the plants in a solution comprising the composition of the invention.

The invention also provides a method to induce in plants systemic resistance to diseases caused by phytopathogenic organisms, which comprises applying an effective amount of the composition of the invention either onto the soil or the plant into which systemic resistance to disease wants to be induced.

The invention also provides a method to control agents which cause biodeterioration of materials, which comprises applying an effective amount of the composition of the invention onto said materials.

The following examples illustrate the invention and should not be considered as limiting in any way, in particular, these examples illustrate the effectiveness of a combination of species object of this invention as compared to (a) chemical fungicides commonly used in protecting beet seeds (Examples 1 to 6), (b) other biological control agents applied commercially in other countries on strawberry crops (Examples 7 and 8), and (c) a single biological control strain belonging to one of the species included in the composition object of the invention (Example 9).

EXAMPLE 1

Effectiveness in the Presence of *Rhizoctonia solani* in Transplanted Sugar Beet A biological control test was performed in sugar beet (*Beta vulgaris*) transplanted (seeds sown in a greenhouse, two months before the normal sowing time, within paper cartridges where the seedlings develop thanks to a nutritive support and adequate warmth and moisture) in a field in which, at least in the past three campaigns, root rot problems caused by the fungus *Rhizoctonia solani* had been detected. The test was carried out between the 4th of May of 1996 (transplant date) and the 17th of Oct. 1996 (date in which the beet roots were pulled from the ground) with seeds of the Ibis variety, in Nava de Arévalo (Avila).

Two treatments were performed:

Treatment 1: seeds pilled with the fungicides thiram and hymexazol, and

Treatment 2: seeds pilled with the fungicides thiram and hymexazol, to which a mixture of five strains of the genus *Trichoderma* was applied, corresponding to the species *T. inhamatum* (1 strain), *T. atroviride* (2 strains) and *T. asperellum* (2 strains). The application of the mixture of the three species of *Trichoderma* was carried out by means of four pulverisations of 6 l/Ha and 20 million conidia of each strain/ml, performed every fifteen days during the months following the date of transplantation.

The productivity study was as follows:

Treatment 1 presented 56,300 roots/Ha, 36.7 Tm of roots/Ha, 16.1% polarisation and 5,915 Kg of sugar/Ha, whereas Treatment 2 presented 56,300 roots/Ha, 41.8 Tm of roots/Ha, 16.5% polarisation and 6,884 Kg of sugar/Ha; and the variation in production of Treatment 2 with respect to Treatment 1 was: Roots/Ha: 0%, Tm of roots/Ha: +13.9%, Percentage polarisation: +2.5% and Kg sugar/Ha: +16.4%.

EXAMPLE 2

Effectiveness in the Presence of *Rhizoctonia solani* in Transplanted Sugar Beet.

A biological control test was performed in sugar beet (*Beta vulgaris*) transplanted (seeds sown in a greenhouse, two months before the normal sowing time, within paper cartridges where the seedlings develop thanks to a nutritive support and adequate warmth and moisture) in a field in which, at least in the past three campaigns, root rot problems caused by the fungus *Rhizoctonia solani* had been detected. The test was carried out between the 2nd of Apr. of 1997 (transplant date) and the 28th of Aug. 1997 (date in which the beet roots were pulled from the ground) with seeds of the Riposte variety, in Nava de Arévalo (Avila).

Two treatments were performed:

Treatment 1: seeds pilled with the fungicides thiram and hymexazol, and

Treatment 2: seeds pilled with the fungicides thiram and hymexazol, to which a mixture of five strains of the genus *Trichoderma* was applied, corresponding to the species *T. inhamatum* (1 strain), *T. atroviride* (2 strains) and *T. asperellum* (2 strains). The application of the mixture of the three species of *Trichoderma* was carried out by means of four pulverisations of 6 l/Ha and 20 million conidia of each strain/ml, performed on days 2 Apr. 1997, 4 May 1997, 3 Jun. 1997 and 3 Jul. 1997.

The productivity study was as follows:

Treatment 1 presented 58,500 roots/Ha, 61.7 Tm of roots/Ha, 13.6% polarisation and 8,262 Kg of sugar/Ha;

Treatment 2 presented 52,000 roots/Ha, 70.5 Tm of roots/Ha, 12.8% polarisation and 9,004 Kg of sugar/Ha;

the variation in production of Treatment 2 with respect to Treatment 1 was: Roots/Ha: −10.7%, Tm of roots/Ha: +15.4%, Percentage polarisation: −5.6% and Kg sugar/Ha: +9%; and the economic yield was of 6.6% in favour of Treatment 2.

EXAMPLE 3

Effectiveness in the Presence of *Rhizoctonia solani* in Traditionally Sown Sugar Beet with Application of *Trichoderma* Covering the Seeds.

A biological control test was performed in sugar beet (*Beta vulgaris*) in a field in which, at least in the past three campaigns, root rot problems caused by the fungus *Rhizoctonia solani* had been detected. The test was carried out between the 5th of Apr. of 1998 (sowing date) and the 14th of Oct. 1998 (date in which the beet roots were pulled from the ground) with seeds of the Riposte variety, in Nava de Arévalo (Avila).

Three treatments were performed:

Treatment 1: seeds pilled with the fungicides thiram and hymexazol;

Treatment 2: seeds pilled with a mixture of five strains of the genus *Trichoderma* corresponding to the species *T. inhamatum* (1 strain), *T. atroviride* (2 strains) and *T. asperellum* (2 strains). The application of the mixture of the three species of *Trichoderma* was carried out at a concentration of 80,000 conidia of each strain per seed; and Treatment 3: application by sprinkling, on naked seeds (without pilling with any chemical or biological pesticide), of the same mixture of five strains corresponding to the three species of the genus *Trichoderma* which were used in Treatment 2. Four pulverisations were carried out of 6 l/Ha and 20 million conidia of each strain/ml, performed every fifteen days during the first two months of cultivation.

The productivity study was as follows:

Treatment 1 presented 45,333 roots/Ha, 27.2 Tm of roots/Ha, 14.7% polarisation and 3,978 Kg of sugar/Ha;

Treatment 2 presented 56,000 roots/Ha, 38.5 Tm of roots/Ha, 14.1% polarisation and 5,441 Kg of sugar/Ha;

Treatment 3 presented 50,000 roots/Ha, 28.7 Tm of roots/Ha, 14.8% polarisation and 4,237 Kg of sugar/Ha;

the variation in production of Treatment 2 with respect to Treatment 1 was: Roots/Ha: +23.5%, Tm of roots/Ha: +41.5%, Percentage polarisation: −4.1% and Kg sugar/Ha: +36.8%;

the variation in production of Treatment 3 with respect to Treatment 1 was: Roots/Ha: +10.3%, Tm of roots/Ha: +5.5%, Percentage polarisation: +0.7% and Kg sugar/Ha: +6.5%; and the economic yield was of 43.5% in favour of Treatment 3 and of 6.7% in favour of Treatment 2.

EXAMPLE 4

Effectiveness in Traditionally Sown Sugar Beet, in Fields Infected with the Rhizomania Virus A biological control test was performed in sugar beet (*Beta vulgaris*) in a field in which, at least in the past three campaigns, rhizomania problems [a disease caused by the Beet Necrotic Yellow Vein Furovirus (BNYVV), which in turn is transmitted by the fungus *Polymyxa betae*] had been detected. The test was carried out between the 19th of Apr. of 1996 (sowing date) and the 17th of Oct. of 1997 (date in which the beet roots were pulled from the ground) with seeds of the Riposte variety, in Nava de Arévalo (Avila).

Two treatments were performed:

Treatment 1: seeds pilled with the fungicides thiram and hymexazol, and

Treatment 2: seeds pilled with the fungicides thiram and hymexazol, to which a mixture of five strains of the genus *Trichoderma* was applied, corresponding to the species *T. inhamatum* (1 strain), *T. atroviride* (2 strains) and *T. asperellum* (2 strains). The application of the mixture of the three species of *Trichoderma* was carried out by means of four pulverisations of 6 l/Ha and 20 million conidia of each strain/ml, performed every fifteen days after the sowing date.

The productivity study was as follows:

Treatment 1 presented 63,700 roots/Ha, 58.6 Tm of roots/Ha, 16.4% polarisation and 9,658 Kg of sugar/Ha;

Treatment 2 presented 69,630 roots/Ha, 73.4 Tm of roots/Ha, 16.9% polarisation and 12,406 Kg of sugar/Ha;

the variation in production of Treatment 2 with respect to Treatment 1 was: Roots/Ha: +9.3%, Tm of roots/Ha: +25.3%, Percentage polarisation: +3% and Kg sugar/Ha: +28.5%; and the economic yield was of 28.9% in favour of Treatment 2.

EXAMPLE 5

Effectiveness in Transplanted Sugar Beet in Fields Infected with the Rhizomania virus.

Low Production Conditions

A biological control test was performed in sugar beet (*Beta vulgaris*) transplanted (seeds sown in a greenhouse, two months before the normal sowing time, within paper cartridges where the seedlings develop thanks to a nutritive support and adequate warmth and moisture) in a field in which, at least in the past three campaigns, rhizomania problems (a disease caused by BNYVV, which in turn is transmitted by the fungus *Polymyxa betae*) had been detected. The test was carried out between the 19th of Mar. of 1997 (transplant date) and the 27th of Aug. 1997 (date in which the beet roots were pulled from the ground) with seeds of the Riposte variety, in two fields of Nava de Arévalo (Avila).

Two treatments were performed:

Treatment 1: seeds pilled with the fungicides thiram and hymexazol, and

Treatment 2: seeds pilled with the fungicides thiram and hymexazol, to which a mixture of five strains of the genus *Trichoderma* was applied, corresponding to the species *T. inhamatum* (1 strain), *T. atroviride* (2 strains) and *T. asperellum* (2 strains). The application of the mixture of the three species of *Trichoderma* was carried out by means of four pulverisations of 6 l/Ha and 20 million conidia of each strain/ml, performed on days 20 Mar. 1997, 22 Apr. 1997, 21 May 1997 and 27 Jun. 1997.

Field 1: The productivity study was as follows:

Treatment 1 presented 55,200 roots/Ha, 59.5 Tm of roots/Ha, 16.2% polarisation and 9,674 Kg of sugar/Ha;

Treatment 2 presented 59,200 roots/Ha, 60 Tm of roots/Ha, 16.4% polarisation and 9,830 Kg of sugar/Ha;

the variation in production of Treatment 2 with respect to Treatment 1 was: Roots/Ha: +7.2%, Tm of roots/Ha: +0.8%, Percentage polarisation: +1.2% and Kg sugar/Ha: +1.6%;

the economic yield was of 1.6% in favour of Treatment 2.

Field 2: The productivity study was as follows:

Treatment 1 presented 55,200 roots/Ha, 59.5 Tm of roots/Ha, 16.2% polarisation and 9,674 Kg of sugar/Ha;

Treatment 2 presented 59,200 roots/Ha, 66.5 Tm of roots/Ha, 16% polarisation and 10,655 Kg of sugar/Ha. The variation in production of Treatment 2 with respect to Treatment 1 was: Roots/Ha: +7.2%, Tm of roots/Ha: +11.8%, Percentage polarisation: −1.2% and Kg sugar/Ha: +10.1%. The economic yield was of 10.1% in favour of Treatment 2.

EXAMPLE 6

Effectiveness in Transplanted Sugar Beet in Fields Infected with the Rhizomania Virus.

High Production Conditions

A biological control test was performed in sugar beet (*Beta vulgaris*) transplanted (seeds sown in a greenhouse, two months before the normal sowing time, within paper cartridges where the seedlings develop thanks to a nutritive support and adequate warmth and moisture) in a field in which, at least in the past three campaigns, rhizomania problems (a disease caused by BNYVV, which in turn is transmitted by the fungus *Polymyxa betae*) had been detected. The test was carried out between the 9th of Apr. of 1997 (transplant date) and the 1st of Sep. 1997 (date in which the beet roots were pulled from the ground) with seeds of the Riposte variety, in Iscar (Valladolid).

Two treatments were performed:

Treatment 1: seeds pilled with the fungicides thiram and hymexazol, and

Treatment 2: seeds pilled with the fingicides thiram and hymexazol, to which a mixture of five strains of the genus *Trichoderma* was applied, corresponding to the species *T. inhamatum* (1 strain), *T. atroviride* (2 strains) and *T. asperellum* (2 strains). The application of the mixture of the three species of *Trichoderma* was carried out by means of four pulverisations of 6 l/Ha and 20 million conidia of each strain/ml, performed on 9 Apr. 1997, 13 May 1997, 3 Jun. 1997 and 4 Jul. 1997.

The productivity study was as follows:

Treatment 1 presented 73,500 roots/Ha, 75.7 Tm of roots/Ha, 14.8% polarisation and 11,152 Kg of sugar/Ha;

Treatment 2 presented 76,500 roots/Ha, 82.2 Tm of roots/Ha, 14.9% polarisation and 12,232 Kg of sugar/Ha;

the variation in production of Treatment 2 with respect to Treatment 1 was: Roots/Ha: +4.1%, Tm of roots/Ha: +8.6%, Percentage polarisation: +0.7% and Kg sugar/Ha: +9.7%; and the economic yield was of 9.9% in favour of Treatment 2.

EXAMPLE 7

Effectiveness Upon Immersion of Strawberry Mother Plants in Plant Production Nurseries During the 1999 campaign, biological control tests with strains of the genus *Trichoderma* were performed in high altitude nurseries dedicated to the commercial production of strawberry plants. Two localities were chosen: Field 1: Navalmanzano (Segovia) and Field 2: Santervás de la Vega (Palencia). The application of the biological control agents was done by immersion. The strawberry cultivar used was Camarosa with a sowing frame of 22,220 plants/Ha, at a distance of 1.5×0.3 m in Santervás de la Vega, and 12,120 plants/Ha at a distance of 1.5×0.55 m in Navalmanzano. The design was one of randomised blocks with four repetitions in each treatment and elemental plots of 15 m2 in Santervás de la Vega and of 22.5 m2 in Navalmanzano. The assays were performed in the absence of pathogens, on previously brominated fields, with the object of discovering the effect corresponding to the action of a mixture of strains of three species of *Trichoderma* as a plant growth enhancing agent, as compared with other two commercial formulations (Rootshield Drench and Trichodex) which contained a single strain.

The tests of effectiveness and selectivity of the three *Trichoderma* formulations were carried out by means of the following treatments:

Treatment 1: a mixture of five strains of the genus *Trichoderma* corresponding to the species *T. inhamatum* (1 strain), *T. atroviride* (2 strains) and *T. asperellum* (2 strains), at single doses with 10 ml/l of a suspension of conidia at a concentration of 100 million/ml;

Treatment 2: single dose of the commercial product Rootshield Drench (Bioworks, Geneva, USA) consisting of 22.7 g/l of a wettable powder of the strain *T. harzianum* T22 at a concentration of 10 million conidia/g;

Treatment 3: single dose of the commercial product Trichodex (Volcani Center, Bet Dagan, Israel) consisting of 1.5 g/l of a wettable powder of the strain *T. harzianum* T39 at a concentration of 1,000 million conidia/g;

Treatment 4: the mixture of strains of treatment 1 at double the dose (20 ml/l);

Treatment 5: Rootshield Drench at double the dose (45.4 g/l);

Treatment 6: Trichodex at double the dose (3 g/l); and

Treatment 7: Untreated control.

Field 1 (Navalmanzano): Was sown in sandy soil on the 6th of May of 1999 and was harvested when more than 150 daughter plants per square meter were achieved. The scorings of the number of daughters/plant, carried out 43 days after sowing, are shown in Table 1.

TABLE 1

Immersion test in Navalmanzano, results at 43 days of culture

| Treatment | Leaves/plant* | Runners/plant | Daughters/plant |
|---|---|---|---|
| 1 | 7.2 c | 3.0 c | 0.8ab |
| 2 | 6.4 ab | 2.4 b | 0.7 ab |
| 3 | 7.2 c | 2.4 b | 0.8 ab |
| 4 | 6.8 bc | 2.4 b | 1.3 c |
| 5 | 6.8 bc | 2.5 b | 0.8 ab |
| 6 | 6.7 bc | 2.6 bc | 0.8 ab |
| 7 | 6.0 a | 1.8 a | 0.6 a |

*The values of each column followed by a same letter do not differ significantly (ANOVA, $p < 0.05$).

Treatment 1 was significantly superior to the control, by 20% in terms of number of leaves/plants, 63% in number of premium runners/plant and by 81% in terms of daughters/plant. Regarding the other treatments with simple doses of *Trichoderma*, Treatment 1 was 14% superior to Treatment 2 in terms of number of leaves/plant, 35% in number of premium runners/plant and by 53% in terms of daughters/plant. Likewise, Treatment 1 was 34% superior to Treatment 3 in terms of number of first-class runners/plant and by 32% in terms of daughters/plant.

Treatment 4 was significantly superior to the control by 13% in terms of leaves/plant and by 138% in number of daughters/plant. Regarding the other treatments performed at double the dose, Treatment 4 was not significantly superior to Treatments 5 and 6 in terms of number of leaves and premium runners/plant. However, it did surpass them by 89% in the number of daughters/plant.

After 90 days had elapsed from the sowing of the crop, the number of daughters having more than three leaves was significantly superior in treatments 1, 3, 4 and 5 with respect to Treatment 7 (Table 2). Treatments 1 and 4 were, respectively, 76% and 54% superior to the untreated control, in terms of the number of daughters with more than three leaves and in terms of total number of daughter.

TABLE 2

Immersion assay in Navalmanzano, results at 90 days of culture

| Treatment | Daughters > 3 leaves/m2* | Total No. daughters/m2 |
|---|---|---|
| 1 | 93 c | 162 c |
| 2 | 69 ab | 139 bc |
| 3 | 89 bc | 149 bc |
| 4 | 81 bc | 142 bc |
| 5 | 76 bc | 138 bc |
| 6 | 69 ab | 125 ab |
| 7 | 53 a | 103 a |

*The values of each column followed by a same letter do not differ significantly (ANOVA, $p < 0.05$).

Treatment 1 was significantly superior to Rootshield Drench, at single doses, in terms of number of daughters with more than three leaves, by 46% with respect to the control and by 8% to Trichodex with respect to the control. The mixture of *Trichoderma* was also superior to the other two treatments, at single doses, in terms of total number of daughters: 23% and 13% with respect to Treatments 2 and 3.

At double the dose, Treatment 4 was not significantly superior, but did reach higher values than those corresponding to the number of daughters with more than three leaves and to the total number of daughters in Treatments 5 and 6.

Field 2 (Santervás de la Vega): Was sown in clayey soil on the 5th of May of 1999 and was harvested when more than 135 daughter plants per square meter were achieved. The scores of the number of flowers/plant and number of commercial daughters per square meter, carried out respectively, 42 and 161 days after sowing, are shown in Table 3.

TABLE 3

Immersion test in Santervás de la Vega, results of production of flowers/plant, 42 days after culture, and of commercial daughters/m2 161 days after sowing.

| Treatment | Flowers/plant (42 d)* | Commercial daughters/m2 (161 d) |
|---|---|---|
| 1 | 3.4 bc | 72 ab |
| 2 | 1.8 a | 94 b |
| 3 | 2.7 ab | 69 ab |
| 4 | 4.1 c | 92 b |
| 5 | 4.2 c | 75 ab |
| 6 | 4.4 c | 88 b |
| 7 | 3.7 bc | 53 a |

*The values of each column followed by a same letter do not differ significantly (ANOVA, $p < 0.05$).

In this field the double doses resulted in better results than single doses, and the behaviour of the three Trichoderma formulations was very alike. It is remarkable that in the production of commercial daughter plants, the mixture of Trichoderma is superior to Rootshield Drench and Trichodex, at double the doses, by 33% and 8% with respect to the control.

EXAMPLE 8

Effectiveness on Pulverisation of Strawberry Mother Plants in Plant Production Nurseries During the 1999 campaign, biological control tests with strains of the genus *Trichoderma* were preformed in high altitude nurseries dedicated to the commercial production of strawberry plants. Two localities were chosen: Field 1: Navalmanzano (Segovia) and Field 2: Santervás de la Vega (Palencia). The application of the biological control agents was done by pulverisation on the sowing day (22 Jun. 1999) and after 45 days (6 Aug. 1999). The strawberry cultivar used was Camarosa with a sowing frame of 22,220 plants/ Ha, at a distance of 1.5×0.3 m in Santervás de la Vega, and 12,120 plants/Ha at a distance of 1.5×0.55 m in Navalmanzano. The design was one of randomised blocks with four repetitions in each treatment and elemental plots of 15 m2 in Santervás de la Vega and of 22.5 m2 in Navalmanzano. The assays were performed in the absence of pathogens, on previously methyl bromide-treated fields, with the object of discovering the effect corresponding to the action of a mixture of strains of three species of *Trichoderma* as a plant growth enhancing agent, as compared with the commercial formulations Trichodex which contains the strain *T. harzianum* T39 of well known effectiveness in this kind of application.

Field 1 (Navalmanzano): Was sown in sandy soil on the 22nd of Jun. of 1999 and was harvested on the 18th of Oct. of 1999. The effectiveness and selectivity tests of the two *Trichoderma* formulations were carried out by means of the following treatments:

Treatment 1: a mixture of five strains of the genus *Trichoderma* corresponding to the species *T. inhamatum* (1 strain), *T. atroviride* (2 strains) and *T. asperellum* (2 strains), at single doses of 6.3 ml/l of a suspension of conidia at a concentration of 100 million/ml;

Treatment 2: single dose of the commercial product Trichodex (Volcani Center, Bet Dagan, Israel) consisting of 4.3 Kg/Ha of a wettable powder of the strain *T. harzianum* T39 at a concentration of 1,000 million conidia/g;

Treatment 3: the mixture of strains of treatment 1 at double the dose (12.3 l/Ha);

Treatment 4: Trichodex at double the dose (7.8 Kg/Ha); and

Treatment 5: Untreated control.

In the case of the first four treatments, reminder doses were applied 45 days after the first one, at the following concentrations: Treatment 1: 5.8 l/Ha; Treatment 2: 3.9 Kg/Ha; Treatment 3: 12.2 l/Ha; and Treatment 4: 8 Kg/Ha.

The scoring of the number of daughters per square meter did not reveal significant differences between the two formulations. The greater precocity of the effects on the growth of the strawberry plants obtained with the *Trichoderma* mixture was compensated along the cultivation period (Tables 4 and 5). However, the final plant production values were superior with the mixture of *Trichoderma* by 3% at a single dose and by 2% at double the dose.

TABLE 4

Pulverisation assay in Navalmanzano, results at 28 days of culture

| Treatment | Daughters > 2 leaves/m2 (28 d)* | Total daughters/m2 (48 d) |
|---|---|---|
| 1 | 18 | 29 |
| 2 | 15 | 26 |
| 3 | 15 | 25 |
| 4 | 14 | 25 |
| 5 | 15 | 24 |

*There are no significant differences between treatments.

TABLE 5

Pulverisation assay in Navalmanzano, results at 48 days of culture

| Treatment | Daughters > 2 leaves/m2 (28 d)* | Total daughters/m2 (48 d) |
|---|---|---|
| 1 | 30 | 62 |
| 2 | 35 | 65 |
| 3 | 36 | 73 |
| 4 | 39 | 77 |
| 5 | 30 | 61 |

The analysis of production of commercial plants, measured in terms of diameter of the crown, dry weight of petioles and leaves, and dry weight of the roots yielded significant differences in all the treatments, except Trichodex at a single dose, with respect to the untreated control. The best results were achieved with the mixture of *Trichoderma* at double the dose (Table 6).

TABLE 6

Pulverisation test in Navalmanzano, results of crown diameter (mm) and dry weight (g)/plant at the end of the experiment

| Treatment | Crown (mm)* | Leaves and petioles (g) | Root (g) |
|---|---|---|---|
| 1 | 10.875 bc | 2.421 | 1.283 |
| 2 | 9.171 ab | 1.984 | 1.238 |
| 3 | 11.375 c | 2.441 | 1.640 |
| 4 | 10.700 bc | 2.035 | 1.555 |
| 5 | 8.337 a | 1.116 | 0.747 |

*The values of each column followed by a same letter do not differ significantly (ANOVA, $p < 0.05$).

The values of the three physiological development parameters considered were superior when the *Trichoderma* mixture was used.

Field 2 (Santervás de la Vega): Was sown in clayey soil on the 24th of Jun. of 1999 and was harvested on the 5th of Nov. of 1999. The effectiveness and selectivity tests of the two *Trichoderma* formulations were carried out by means of the following treatments:

Treatment 1: a mixture of five strains of the genus *Trichoderma* corresponding to the species *T. Inhamatum* (1 strain), *T. atroviride* (2 strains) and *T. asperellum* (2 strains), at single doses of 6.4 ml/l of a suspension of conidia at a concentration of 100 million/ml;

Treatment 2: single dose of the commercial product Trichodex (Volcani Center, Bet Dagan, Israel consisting of 4.2 Kg/Ha of a wettable powder of the strain *T. harzianum* T39 at a concentration of 1,000 million conidia/g;

Treatment 3: the mixture of strains of treatment 1 at double the dose (12.5 l/Ha);

Treatment 4: Trichodex at double the dose (8.1 Kg/Ha);

Treatment 5: Untreated control.

In the case of the first four treatments, reminder doses were applied at 45 days after the first one, at the following concentrations: Treatment 1: 6.2 l/Ha; Treatment 2: 4.3 Kg/Ha; Treatment 3: 12.3 l/Ha; and Treatment 4: 8.4 Kg/Ha.

As in the case of Field 1, no significant differences were detected in precocity or in number of daughter plants and commercial plants, between the treatments. However, significant differences were observed in the physiological development parameters of the strawberry plants at the end of the cultivation period (Table 7).

TABLE 7

Pulverisation test in Santervás de la Vega, results of crown diameter (mm) and dry weight (g)/plant at the end of the experiment

| Treatment | Crown (mm)* | Leaves and petioles (g) | Root (g) |
| --- | --- | --- | --- |
| 1 | 11.275 ab | 2.680 | 1.904 |
| 2 | 11.325 ab | 3.107 | 2.039 |
| 3 | 12.150 b  | 3.427 | 2.228 |
| 4 | 11.475 a  | 2.557 | 2.219 |
| 5 | 11.625 a  | 1.936 | 1.998 |

*The values of each column followed by a same letter do not differ significantly (ANOVA, $p < 0.05$).

As in case of Field 1, the maximum values were achieved in the treatment with the double dose *Trichoderma* mixture.

EXAMPLE 9

Effectiveness in the Biological Control of Fungal Melon Collapse

The fungal disease known as "melon collapse" or "sudden death of the melon" is characterised by radicular injury, which eventually brings about the death of the plant. It is caused by different soil dwelling fungi of which *Acremonium cucurbitacearum* is the most remarkable due to its importance. In an attempt to find a method for the control of this pathogen, a comparative study has been carried out between a formulation containing *Trichoderma inhamatum* (1 strain) and a mixture of three species with *T. atroviride* (1 strain), *T. inhamatum* (1 strain) and *T. asperellum* (2 strains). To perform the assay, an acidic clayey soil was used, which had never been in the presence of melon or of the target pathogen, as well as a sandier, more alkaline soil, with a history of melon and collapse. Both soils were arranged in pots of 15–17 cm diameter and 13–15 cm of height, with capacity for 2 kg of soil.

The innoculum of *A. cucurbitacearum* A419 (Collection of the Polytechnic University of Valencia) was distributed into 2 kg of soil until a concentration of 50,000 colony forming units (CFU)/g of soil was obtained. After 24 h, three pre-germinated melon seeds of the Spanish piel de sapo variety were sown in each pot, at a depth of 2 cm, and 24 h later, the *Trichoderma* formulations were applied. Treatment with *Trichoderma* was carried out diluting Formulation 1 (*T. inhamatum* F534, Czech Collection, Brno) and Formulation 2 (*T. atroviride* IMI 113135, *T. inhamatum* F534 and *T. asperellum* ThVa and T4.4, University of Salamanca) until a concentration of 25,000 CFU/g of soil was obtained for each of them. After a week, only one melon plantule was allowed to remain per pot.

The plants were pulled out after 45 days of being sown, and an evaluation was done of the injuries in the main and in secondary roots using a 0 to 4 scale, according to which 0 corresponds to minimal injury (healthy plant) and 4 to maximum injury (abundant necrosis and greater than 50% reduction in root beard). The results of two experiments: sterile acidic soil with *A. cucurbitacearum*, and sterile alkaline soil with *A. cucurbitacearum* are shown in Tables 8 and 9.

TABLE 8

Assessment of injury in the main root and secondary roots of melon sown in sterilised acidic soil, in a scale ranging from 0 (minimal injury) to 4 (maximum injury), for the following treatments: control (sterilised soil), Acremonium (sterilised soil with *A. cucurbitaceum*), Acremonium + F1 (sterilised soil with *A. cucurbitaceum* and *Trichoderma* Formulation 1) and Acremonium + F2 (sterilised soil with *A. Cucurbitaceum* and *Trichoderma* Formulation 2)

| Treatment | Main root* | Secondary roots |
| --- | --- | --- |
| Control | 0.0 ± 0.0 a | 0.0 ± 0.0 a |
| Acremonium | 1.0 ± 0.0 b | 1.0 ± 0.0 b |
| Acremonium + F1 | 0.5 ± 0.6 ab | 0.5 ± 0.6 ab |
| Acremonium + F2 | 0.3 ± 0.5 a | 0.3 ± 0.5 a |

*The values of each column followed by a same letter do not differ significantly (ANOVA, $p < 0.05$).

TABLE 9

Assessment of injury in the main root and secondary roots of melon sown in sterilised alkaline soil, in a scale ranging from 0 (minimal injury) to 4 (maximum injury), for the following treatments: control (sterilised soil), Acremonium (sterilised soil with *A. cucurbitaceum*), Acremonium + F1 (sterilised soil with *A. cucurbitaceum* and *Trichoderma* Formulation 1) and Acremonium + F2 (sterilised soil with *A. Cucurbitaceum* and *Trichoderma* Formulation 2)

| Treatment | Main root* | Secondary roots |
| --- | --- | --- |
| Control | 0.0 ± 0.0 a | 0.0 ± 0.0 a |
| Acrernonium | 3.5 ± 0.6 b | 4.0 ± 0.0 b |
| Acremonium + F1 | 2.5 ± 1.3 b | 3.0 ± 1.2 c |
| Acremonium + F2 | 0.8 ± 0.5 a | 1.5 ± 0.6 ac |

*The values of each column followed by a same letter do not differ significantly (ANOVA, $p < 0.05$).

Tables 8 and 9 reveal that Formulation 2, composed of a combination of three species of *Trichoderma*, perform a better control of the artificially inoculated pathogen than Formulation 1. In the four cases shown in the two tables, Formulation 2 achieved a significant control of the pathogen.

We claim:

1. A composition comprising a mixture of fungi of the genus *Trichoderma* belonging to, at least two different species selected from *Trichoderma asperellum*, *Trichoderma atroviride*, and *Trichoderma inhamatum*.

2. Composition according to claim 1, which comprises a mixture of fungi belonging to the species *Trichoderma asperellum*, *Trichoderma acroviride*, and *Trichoderma inhamatum*.

3. Composition according to claim 1 which further comprises one or more additional biological control agents which are not incompatible with the fungi present in said composition.

4. Composition according to claim 1, in a solid presentation form.

5. Composition according to claim 1, in a liquid presentation form.

6. A method for protecting or treating plants and plant material against infections and diseases caused by phytopathogenic organisms, which comprises applying an effective amount of a composition according to claim 1, onto soil or on a plant or plant material to be protected or treated.

7. A method to stimulate plant growth which comprises applying an effective amount of a composition according to claim 1, on the soil or on the plant the growth of which wants to be stimulated.

8. A method to induce in plants systemic resistance to diseases caused by phytopathogenic organisms which comprises applying an effective amount of a composition according to claim 1, onto the soil or on the plant into which systemic resistance to diseases is to be induced.

9. A method for controlling biodeterioration agents of materials which comprises applying an effective amount of a composition according to claim 1, onto said materials.

* * * * *